United States Patent
Nakashima et al.

(12)

(10) Patent No.: US 6,369,279 B1
(45) Date of Patent: Apr. 9, 2002

(54) STYRENE DERIVATIVES

(75) Inventors: Mutsuo Nakashima; Jun Hatakeyama; Jun Watanabe; Yuji Harada, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/657,515

(22) Filed: Sep. 7, 2000

(30) Foreign Application Priority Data

Sep. 8, 1999 (JP) .......................... 11-253930

(51) Int. Cl.$^7$ .................. C07C 43/12; C07C 43/20; C07C 22/08
(52) U.S. Cl. .................. 568/630; 568/656; 570/127
(58) Field of Search ................ 568/630, 656; 570/127

(56) References Cited

U.S. PATENT DOCUMENTS

| | | | |
|---|---|---|---|
| 4,491,628 A | 1/1985 | Ito et al. | |
| 5,843,624 A | 12/1998 | Houlihan et al. | |
| 5,968,713 A | 10/1999 | Nozaki et al. | |
| 5,998,099 A | 12/1999 | Houlihan et al. | |
| 6,013,416 A | 1/2000 | Nozaki et al. | |

FOREIGN PATENT DOCUMENTS

| | | | |
|---|---|---|---|
| JP | 62289539 A2 | * | 12/1987 |
| JP | 63-27829 | | 2/1988 |
| JP | 2-27660 | | 6/1990 |
| JP | 9-73173 | | 3/1997 |
| JP | 9-230595 | | 9/1997 |
| JP | 10-10739 | | 1/1998 |
| WO | 97/33198 | | 9/1997 |

OTHER PUBLICATIONS

Yamaguchi et al. "Ortho–Vinylation Reaction of Phenols with Ethyne". Journal of Organic Chemistry (1998), 63(21), 7298–7305. See abstract.*
Sahlberg et al. Synthesis of anti–HIV activities of urea–PETT anologs belonging to a new class of potent non–nuncleoside HIV–1 reverse transcriptase inhibitors. Bioorg. Med. Chem. Lett. (1998), 8(12), 1511–1516. See Abstract.*
Aldrich Chemical Company, Inc. (1996) p 1527, cat# 14, 100–3.*
English abstract for JP 9–230595.

* cited by examiner

Primary Examiner—Sreeni Padmanabhan
Assistant Examiner—Sikarl A. Witherspoon
(74) Attorney, Agent, or Firm—Millen, White, Zelano & Branigan, P.C.

(57) ABSTRACT

Styrene derivatives of formula (1) are novel wherein $R^1$ is hydrogen, $C_{1-20}$ alkyl, fluoro-substituted $C_{1-20}$ alkyl, chloro, or trichloromethyl, $R^2$ is a phenol protecting group, p, q and r are integers in the range of $0 \leq p < 5$, $0 \leq q < 5$, $0 < r < 5$, and $0 < p+q < 5$.

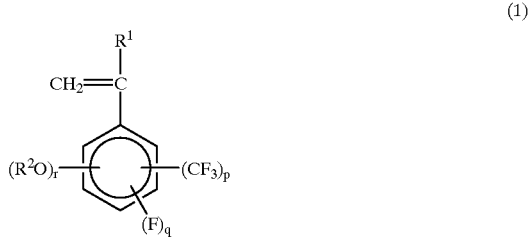

(1)

Polymers obtained by polymerizing the styrene derivatives are useful as the base polymer of resist compositions.

25 Claims, No Drawings

STYRENE DERIVATIVES

This invention relates to novel styrene derivatives which are useful monomers in preparing base polymers for use in chemically amplified resist compositions for microfabrication.

BACKGROUND OF THE INVENTION

In the drive for higher integration and operating speeds in LSI devices, the pattern rule is made drastically finer. The rapid advance toward finer pattern rules is grounded on the development of a projection lens with an increased NA, a resist material with improved performance, and exposure light of a shorter wavelength. In particular, the change-over from i-line (365 nm) to shorter wavelength KrF laser (248 nm) brought about a significant innovation, enabling mass-scale production of 0.18 micron rule devices. To the demand for a resist material with a higher resolution and sensitivity, acid-catalyzed chemical amplification positive working resist materials are effective as disclosed in U.S. Pat. Nos. 4,491,628 and 5,310,619 (JP-B 2-27660 and JP-A 63-27829). They now become predominant resist materials especially adapted for deep UV lithography.

Resist materials adapted for KrF excimer lasers enjoyed early use on the 0.3 micron process, went through the 0.25 micron rule, and currently entered the mass production phase on the 0.18 micron rule. Engineers have started investigation on the 0.15 micron rule, with the trend toward a finer pattern rule being accelerated. A wavelength change-over from KrF to shorter wavelength ArF laser (193 nm) is expected to enable miniaturization of the design rule to 0.13 µm or less. Since conventionally used novolac resins and polyvinylphenol resins have very strong absorption in proximity to 193 nm, they cannot be used as the base resin for resists. To ensure transparency and dry etching resistance, some engineers investigated acrylic and alicyclic (typically cycloolefin) resins as disclosed in JP-A 9-73173, JP-A 10-10739, JP-A 9-230595 and WO 97/33198. With respect to $F_2$ excimer laser (157 nm) which is expected to enable further miniaturization to 0.10 µm or less, more difficulty arises in insuring transparency because it was found that acrylic resins are not transmissive to light at all and those cycloolefin resins having carbonyl bonds have strong absorption.

SUMMARY OF THE INVENTION

An object of the invention is to provide a novel styrene derivative which is useful in the preparation of a base polymer for a chemical amplification resist composition having a high transmittance to vacuum ultraviolet radiation of up to 300 nm, especially $F_2$ excimer laser beam (157 nm), $Kr_2$ excimer laser beam (146 nm), KrAr excimer laser beam (134 nm) and $Ar_2$ excimer laser beam (126 nm).

It has been found that a novel styrene derivative of the following general formula (1) can be obtained by the method to be described later, and that using a resin based on a fluorinated polyhydroxystyrene obtained from the novel styrene derivative, a resist composition having transparency and alkali solubility is formulated.

As long as the inventor has confirmed, polyhydroxystyrene is somewhat improved in transmittance near 160 nm, but to an extent far below the practical level, and reducing carbonyl and carbon-to-carbon double bonds is essential for insuring a transmittance. However, phenols are good in etching resistance and alkali solubility, as compared with acrylic compounds. Further, halogen-substituted phenol polymers, and especially fluorine-substituted polymers obtained from the inventive styrene derivatives are improved in transmittance nearly to the practical level.

The invention provides a styrene derivative of the following general formula (1).

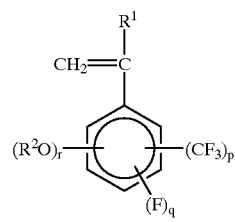

(1)

Herein $R^1$ is hydrogen, a straight, branched or cyclic, unsubstituted or fluoro-substituted alkyl group of 1 to 20 carbon atoms, chlorine atom, or trichloromethyl group, $R^2$ is a phenol protecting group, p, q and r are integers in the range of $0 \leq p < 5$, $0 \leq q < 5$, $0 < r < 5$, and $0 < p+q < 5$.

DESCRIPTION OF THE PREFERRED EMBODIMENT

In formula (1) representative of the novel styrene derivative according to the invention, $R^1$ is hydrogen, a straight, branched or cyclic, unsubstituted or fluoro-substituted alkyl group of 1 to 20 carbon atoms, chlorine atom, or trichloromethyl group. Examples of the straight, branched or cyclic $C_{1-20}$ alkyl group represented by $R^1$ include methyl, ethyl, propyl, isopropyl, n-butyl, sec-butyl, tert-butyl, cyclopentyl, cyclohexyl, 2-ethylhexyl, and n-octyl. The alkyl groups of 1 to 4 carbon atoms are preferred, with methyl being most preferred. The fluorinated alkyl groups are the foregoing alkyl groups in which some or all of the hydrogen atoms are replaced by fluorine atoms, for example, trifluoromethyl, 2,2,2-trifluoroethyl, 3,3,3-trifluoropropyl, and 1,1,2,3,3,3-hexafluoropropyl.

$R^2$ is a protective group on a phenol moiety, which is preferably selected from among methyl, vinyl, allyl, benzyl, and groups of the following general formulae (10), (11), (12), (13) and (14).

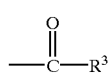

(10)

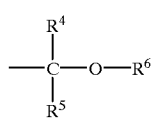

(11)

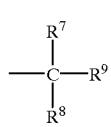

(12)

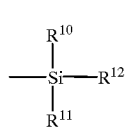

(13)

-continued $$—(CH_2)\overline{_a}\overset{\overset{O}{\|}}{C}—O—R^{13} \quad (14)$$

In formula (10), $R^3$ is a straight, branched or cyclic alkyl group of 1 to 20 carbon atoms. $R^4$ and $R^5$ each are hydrogen, a straight, branched or cyclic alkyl group of 1 to 20 carbon atoms which may contain a hetero atom, $R^6$ is a straight, branched or cyclic alkyl group of 1 to 20 carbon atoms which may contain a hetero atom, aryl, aralkyl or oxoalkyl group, and a pair of $R^4$ and $R^5$, a pair of $R^4$ and $R^6$, or a pair of $R_5$ and $R^6$, taken together, may form a cyclic structure of 3 to 12 carbon atoms. $R^7$, $R^8$ and $R^9$ each are a straight, branched or cyclic alkyl group of 1 to 20 carbon atoms which may contain a hetero atom, aryl, aralkyl or oxoalkyl group, and a pair of $R^7$ and $R^8$, a pair of $R^7$ and $R^9$, or a pair of $R^8$ and $R^9$, taken together, may form a cyclic structure of 3 to 12 carbon atoms. $R^{10}$, $R^{11}$ and $R^{12}$ each are a straight or branched alkyl group of 1 to 4 carbon atoms. $R^{13}$ is a straight, branched or cyclic alkyl group of 1 to 20 carbon atoms which may contain a hetero atom, aryl, aralkyl or oxoalkyl group, and "a" is an integer of 0 to 10.

Examples of the alkyl group represented by $R^3$ are the same as exemplified for $R^1$. Alkyl groups of 1 to 4 carbon atoms are preferred, with methyl being most preferred. Illustrative examples of the group of formula (10) are acetyl, propionyl, butyryl and isobutyryl.

In formula (11), examples of the alkyl group represented by $R^4$, $R^5$ and $R^6$ are the same as exemplified for $R^1$. Alkyl groups of 1 to 8 carbon atoms, especially 1 to 6 carbon atoms are preferred. These alkyl groups may contain a hetero atom such as oxygen, sulfur, nitrogen or fluorine. Examples are alkyl groups which are separated by an oxygen atom, sulfur atom or NH group. Also included are alkyl groups in which some or all of the hydrogen atoms are replaced by fluorine atoms.

A pair of $R^4$ and $R^5$, a pair of $R^4$ and $R^6$, or a pair of $R^5$ and $R^6$, taken together, may form a cyclic structure of 3 to 12 carbon atoms, especially 5 to 10 carbon atoms. Each of $R^4$, $R^5$ and $R^6$ is an alkylene group that forms a cyclic structure having the desired number of carbon atoms, when they form a ring.

Illustrative examples of the group of formula (11) are straight or branched acetal groups such as methoxymethyl, methoxyethoxymethyl, 1-methoxyethyl, 1-ethoxyethyl, 1-n-propoxyethyl, 1-isopropoxyethyl, 1-n-butoxyethyl, 1-isobutoxyethyl, 1-sec-butoxyethyl, 1-tert-butoxyethyl, 1-tert-amyloxyethyl, 1-ethoxy-n-propyl, 1-cyclopentyloxyethyl, 1-cyclohexyloxyethyl, 1-methoxy-n-propyl, ethoxypropyl, 1-methoxy-1-methyl-ethyl, and 1-ethoxy-1-methyl-ethyl. These groups are shown by the following formulae.

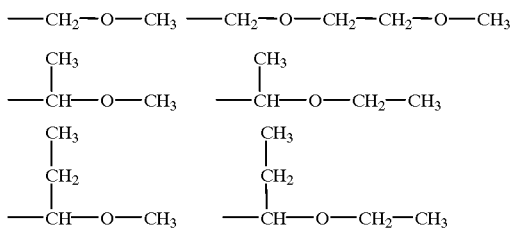

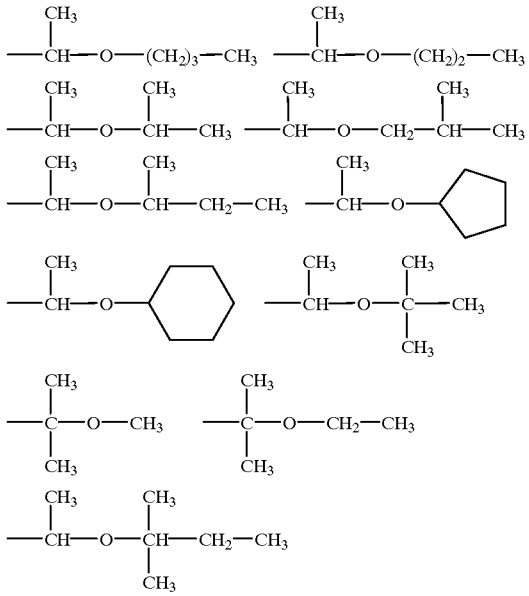

Of the groups represented by formula (11), cyclic groups are, for example, tetrahydrofuran-2-yl, 2-methyltetrahydrofuran-2-yl, tetrahydropyran-2-yl and 2-methyltetrahydropyran-2-yl. Of the groups represented by formula (11), ethoxyethyl, butoxyethyl, and ethoxypropyl are preferred.

In formula (12), examples of the alkyl group represented by $R^7$, $R^8$ and $R^9$ are the same as exemplified for $R^1$. Alkyl groups of 1 to 8 carbon atoms, especially 1 to 6 carbon atoms are preferred. These alkyl groups may contain a hetero atom such as oxygen, sulfur, nitrogen or fluorine. Examples are alkyl groups which are separated by an oxygen atom, sulfur atom or NH group. Also included are alkyl groups in which some or all of the hydrogen atoms are replaced by fluorine atoms.

A pair of $R^7$ and $R^8$, a pair of $R^7$ and $R^9$, or a pair of $R^8$ and $R^9$, taken together, may form a cyclic structure of 3 to 12 carbon atoms, especially 5 to 10 carbon atoms. Each of $R^7$, $R^8$ and $R^9$ is an alkylene group that forms a cyclic structure having the desired number of carbon atoms, when they form a ring.

Illustrative examples of the tertiary alkyl group of formula (12) include tert-butyl, triethylcarbyl, 1-ethylnorbornyl, 1-methylcyclohexyl, 1-ethylcyclopentyl, 2-(2-methyl) adamantyl, 2-(2-ethyl)adamantyl, and tert-amyl.

In formula (13), examples of the alkyl group represented by $R^{10}$, $R^{11}$ and $R^{12}$ are methyl, ethyl, propyl, isopropyl, n-butyl, sec-butyl, and tert-butyl. Illustrative examples of the group of formula (13) include trimethylsilyl, triethylsilyl and tert-butyldimethylsilyl.

In formula (14), examples of the alkyl group represented by $R^{13}$ are the same as exemplified for $R^1$. The hetero atoms which can be contained in these alkyl groups are as exemplified for $R^4$ to $R^9$. Illustrative examples of the group of formula (14) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl, 2-tetrahydrofuranyl-oxycarbonylmethyl, triethylcarbyloxycarbonylmethyl, 1-ethylnorbornyloxycarbonylmethyl, 1-methylcyclohexyloxy-carbonylmethyl, 1-ethylcyclohexyloxycarbonylmethyl, 1-methylcyclopentyloxycarbonylmethyl, 1-ethylcyclopentyl-oxycarbonylmethyl, 2-(2-methyl)adamantyloxycarbonylmethyl, 2-(2-ethyl)adamantyloxycarbonylmethyl, and tert-amyloxy-carbonylmethyl.

Also, $R^6$, $R^7$, $R^8$, $R^9$ and $R^{13}$ stand for substituted or unsubstituted aryl groups of 6 to 20 carbon atoms, for example, phenyl groups, p-methylphenyl, p-ethylphenyl, and alkoxy-substituted phenyl groups such as p-methoxyphenyl, aralkyl groups of 7 to 20 carbon atoms, such as benzyl and phenethyl. Also included are similar alkyl and other groups having an oxygen atom, similar alkyl and other groups in which a hydrogen atom attached to a carbon atom is replaced by a hydroxyl group, and similar alkyl and other groups in which two hydrogen atoms are replaced by an oxygen atom to form a carbonyl group, as shown below.

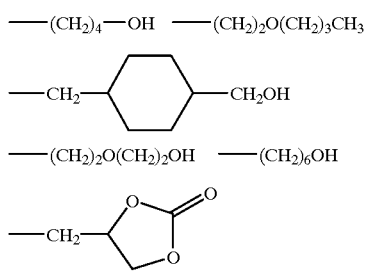

Also $R^6$, $R^7$, $R^8$, $R^9$ and $R^{13}$ stand for oxoalkyl groups of 4 to 20 carbon atoms, for example, 3-oxoalkyl groups and groups as shown below.

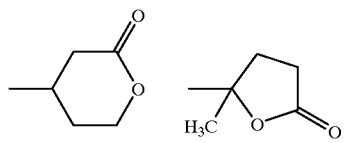

Referring back to formula (1), p, q and r are integers in the range of $0 \leq p < 5$, $0 \leq q < 5$, $0 < r < 5$, and $0 < p+q < 5$. The preferred range is $q \geq 2$, and the more preferred range is $q=2$ and $r=1$.

Accordingly, the styrene derivative of the present invention is preferably of the following general formula (2), more preferably of the following general formula (3), and further preferably of the following general formula (4).

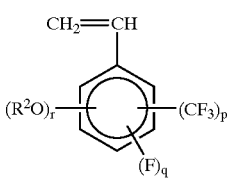
(2)

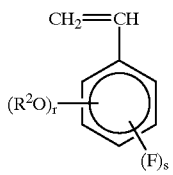
(3)

In formula (3), s is an integer in the range of $0 < s < 5$.

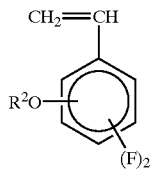
(4)

Of the styrene derivatives, those having the $OR^2$ group at the para position are preferred. Accordingly, the styrene derivatives of the following general formula (5), especially the following general formulae (6) to (8) are preferable.

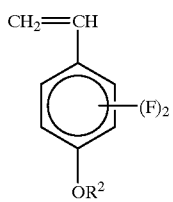
(5)

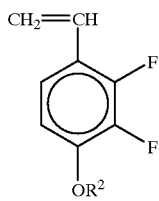
(6)

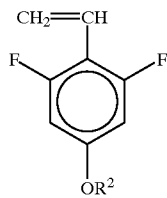
(7)

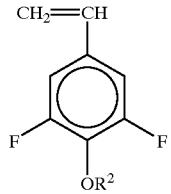
(8)

Also preferred are those styrene derivatives having the $OR^2$ group at the meta position represented by the following general formula (9).

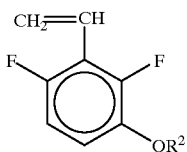

(9)

The styrene derivative of the invention is generally prepared by cross coupling a benzene derivative of the following general formula (1a) with a vinyl derivative of the following general formula (1b).

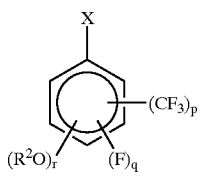

(1a)

$CH_2=CR^1X$ (1b)

Herein, $R^1$, $R^2$, p, q and r are as defined above, and X is a halogen atom, especially bromo or iodo.

In effecting the cross coupling, organometallic compounds are prepared from the compounds of formula (1a) or (1b), examples of the organometallic compounds including organic lithium compounds, organic magnesium compounds, organic zinc compound, organic copper compounds, organic titanium compounds, organic tin compounds and organic boron compounds. Transition metal catalysts such as palladium, nickel and copper catalysts must be used in the cross coupling. Exemplary palladium catalysts include zero-valent palladium compounds such as tetrakis(triphenylphosphine)-palladium(0) and di(1,2-bis (diphenylphosphino)-ethane)palladium(0), divalent palladium compounds such as palladium acetate, palladium chloride, and [1,1'-bis-(diphenylphosphino)ferrocene] palladium(II) chloride, complexes of the divalent palladium compounds with ligands, and combinations of the divalent palladium compounds with reducing agents.

Exemplary nickel catalysts include divalent nickel compounds such as (1,3-bis(diphenylphosphino)propane)nickel chloride (II), (1,2-bis(diphenylphosphino)ethane)nickel chloride (II), and bis(triphenylphosphine)nickel chloride (II), and zero-valent nickel compounds such as tetrakis-(triphenylphosphine)nickel(0).

Exemplary copper catalysts include monovalent copper salts such as copper (I) chloride, copper (I) bromide, copper (I) iodide, and copper (I) cyanide, divalent copper salts such as copper (II) chloride, copper (II) bromide, copper (II) iodide, copper (II) cyanide, and copper (II) acetate, and copper complexes such as dilithium tetracuprate.

Using the styrene derivative of the invention as a monomer, a polymer or high molecular weight compound is prepared. The polymer is generally prepared by mixing the monomer with a solvent, adding a catalyst thereto, and effecting polymerization reaction while heating or cooling the system if necessary. The polymerization reaction depends on the type of initiator or catalyst, trigger means (including light, heat, radiation and plasma), and polymerization conditions (including temperature, pressure, concentration, solvent, and additives). Commonly used for polymerization the styrene derivative of the invention are radical polymerization of triggering polymerization with radicals of α,α'-azobisisobutyronitrile (AIBN) or the like, and ion (anion) polymerization using catalysts such as alkyl lithium. Such polymerization may be effected in a conventional manner.

The polymer thus obtained is used as a base polymer in formulating a resist composition. The resist composition is generally formulated by adding an organic solvent and a photoacid generator to the polymer. If necessary, a crosslinker, basic compound, dissolution inhibitor and the like are added. The resist composition may be prepared in a conventional way.

The resist composition prepared using a polymer obtained by polymerizing the inventive styrene derivative is sensitive to high-energy radiation, has excellent sensitivity and resolution at a wavelength of up to 200 nm, especially up to 170 nm, and excellent plasma etching resistance. The styrene derivative of the invention is an advantageous raw material for a base polymer for formulating a resist composition having a low absorption at the exposure wavelength of a $F_2$ excimer laser. The resulting resist composition is ideal as a micropatterning material in VLSI fabrication since a finely defined pattern having sidewalls perpendicular to the substrate can easily be formed.

EXAMPLE

Examples of the invention are given below by way of illustration and not by way of limitation. AIBN denotes α,α'-azobisisobutyronitrile, and THF denotes tetrahydrofuran.

Example 1

Synthesis of 4-tert-butoxy-2,3-difluorostyrene

A 1-liter reactor was charged with 31.2 g (0.10 mol) of 4-tert-butoxy-2,3-difluoro-1-iodobenzene and 100 ml of THF and heated at 60° C. To the reactor, 1.16 g (1 mmol) of tetrakis(triphenylphosphine)palladium(0) was added, then 120 ml of a THF solution of 1 M vinyl zinc chloride was added dropwise. After the completion of dropwise addition, the reaction solution was ripened for 30 minutes and poured into a saturated ammonium chloride aqueous solution. From the solution, a crude product was extracted with ethyl acetate in a conventional way. It was purified by silica gel chromatography, obtaining 17.6 g (yield 83%) the end product.

IR (v): 2980, 1500, 1470, 1369, 1302, 1161, 1049, 949, 860 (cm$^{-1}$)

$^1$H-NMR: 1.37 ppm 9H (s) 5.37 ppm 1H (d) 5.78 ppm 1H (d) 6.74–6.84 ppm 2H (m) 7.06–7.15 ppm 1H (m)

Example 2

Synthesis of 4-tert-butoxy-2,6-difluorostyrene

The end product was obtained as in Example 1 except that 4-tert-butoxy-2,6-difluoro-1-iodobenzene was used instead of the 4-tert-butoxy-2,3-difluoro-1-iodobenzene.

IR (v): 2981, 1620, 1487, 1369, 1128, 999, 991, 879 (cm$^-$)

$^1$H-NMR: 1.38 ppm 9H (s) 5.47 ppm 1H (d) 5.94 ppm 1H (d) 6.49–6.57 ppm 2H (m) 6.66 ppm 1H (dd)

Example 3

Synthesis of 4-tert-butoxy-3,5-difluorostyrene

The end product was obtained as in Example 1 except that 4-tert-butoxy-3,5-difluoro-1-iodobenzene was used instead of the 4-tert-butoxy-2,3-difluoro-1-iodobenzene.

Example 4

Synthesis of 3-tert-butoxy-2,6-difluorostyrene

The end product was obtained as in Example 1 except that 3-tert-butoxy-2,6-difluoro-1-iodobenzene was used instead of the 4-tert-butoxy-2,3-difluoro-1-iodobenzene.

Example 5

Synthesis of 4-acetoxy-2,3-difluorostyrene

The end product was obtained as in Example 1 except that 4-acetoxy-2,3-difluoro-1-iodobenzene was used instead of the 4-tert-butoxy-2,3-difluoro-1-iodobenzene.

Example 6

Synthesis of 4-(1-ethoxyethyloxy)-2-fluorostyrene

The end product was obtained as in Example 1 except that 4-(1-ethoxyethyloxy)-2-fluoro-1-iodobenzene was used instead of the 4-tert-butoxy-2,3-difluoro-1-iodobenzene.

Example 7

Synthesis of 4-benzyloxy-3-fluoro-α-methylstyrene

The end product was obtained as in Example 1 except that 4-benzyloxy-3-fluoro-1-iodobenzene was used instead of the 4-tert-butoxy-2,3-difluoro-1-iodobenzene and 1-methylvinyl zinc chloride used instead of the vinyl zinc chloride.

Example 8

Synthesis of 2-allyloxy-4-fluoro-α-methylstyrene

The end product was obtained as in Example 1 except that 2-allyloxy-4-fluoro-1-iodobenzene was used instead of the 4-tert-butoxy-2,3-difluoro-1-iodobenzene and 1-methylvinyl zinc chloride used instead of the vinyl zinc chloride.

Example 9

Synthesis of 3-vinyloxy-4-fluorostyrene

The end product was obtained as in Example 1 except that 3-vinyloxy-4-fluoro-1-iodobenzene was used instead of the 4-tert-butoxy-2,3-difluoro-1-iodobenzene.

Example 10

Synthesis of 2-(tert-butyldimethylsilyloxy)-5-fluorostyrene

The end product was obtained as in Example 1 except that 2-(tert-butyldimethylsilyloxy)-5-fluoro-1-iodobenzene was used instead of the 4-tert-butoxy-2,3-difluoro-1-iodobenzene.

Example 11

Synthesis of 4-(2-tetrahydropyranyloxy)-2,3,5,6-tetrafluoro-styrene

The end product was obtained as in Example 1 except that 4-(2-tetrahydropyranyloxy)-2,3,5,6-tetrafluoro-1-iodobenzene was used instead of the 4-tert-butoxy-2,3-difluoro-1-iodobenzene.

Example 12

Synthesis of 3-tert-butoxycarbonyloxy-2-fluorostyrene

The end product was obtained as in Example 1 except that 3-tert-butoxycarbonyloxy-2-fluoro-1-iodobenzene was used instead of the 4-tert-butoxy-2,3-difluoro-1-iodobenzene.

Example 13

Synthesis of 2-acetoxy-6-fluorostyrene

The end product was obtained as in Example 1 except that 2-acetoxy-6-fluoro-1-iodobenzene was used instead of the 4-tert-butoxy-2,3-difluoro-1-iodobenzene.

Example 14

Synthesis of 3-methoxymethyloxy-4-fluorostyrene

The end product was obtained as in Example 1 except that 3-methoxymethyloxy-4-fluoro-1-iodobenzene was used instead of the 4-tert-butoxy-2,3-difluoro-1-iodobenzene.

Example 15

Synthesis of 4-(1-ethylcyclopentyloxycarbonylmethyloxy)-2,6-difluorostyrene

The end product was obtained as in Example 1 except that 4-(1-ethylcyclopentyloxycarbonylmethyloxy)-2,6-difluoro-1-iodobenzene was used instead of the 4-tert-butoxy-2,3-difluoro-1-iodobenzene.

Example 16

Synthesis of 2-acetoxy-4,5,6-trifluoro-α-methylstyrene

The end product was obtained as in Example 1 except that 2-acetoxy-4,5,6-trifluoro-1-iodobenzene was used instead of the 4-tert-butoxy-2,3-difluoro-1-iodobenzene and 1-methylvinyl zinc chloride used instead of the vinyl zinc chloride.

Example 17

Synthesis of 3-tert-butoxy-2,4,6-trifluorostyrene

The end product was obtained as in Example 1 except that 3-tert-butoxy-2,4,6-trifluoro-1-iodobenzene was used instead of the 4-tert-butoxy-2,3-difluoro-1-iodobenzene.

Example 18

Synthesis of 3-tert-butoxy-4,5,6-trifluorostyrene

The end product was obtained as in Example 1 except that 3-tert-butoxy-4,5,6-trifluoro-1-iodobenzene was used instead of the 4-tert-butoxy-2,3-difluoro-1-iodobenzene.

Example 19

Synthesis of 3-acetoxy-4-trifluoromethylstyrene

The end product was obtained as in Example 1 except that 3-acetoxy-4-trifluoromethyl-1-iodobenzene was used instead of the 4-tert-butoxy-2,3-difluoro-1-iodobenzene.

Example 20

Synthesis of 4-tert-butoxy-2,3,5,6-tetrafluorostyrene

The end product was obtained as in Example 1 except that 4-tert-butoxy-2,3,5,6-tetrafluoro-1-iodobenzene was used instead of the 4-tert-butoxy-2,3-difluoro-1-iodobenzene.

IR (ν): 2981, 1514, 1485, 1371, 1140, 1080, 968, 941 (cm$^{-1}$)

$^1$H-NMR: 1.41 ppm 9H (s) 5.65 ppm 1H (d) 6.06 ppm 1H (d) 6.66 ppm 1H (dd)

Example 21

Synthesis of 4-tert-butoxy-2,3-difluoro-α-trifluoromethyl-styrene

The end product was obtained as in Example 1 except that 1-trifluoromethylvinyl zinc chloride was used instead of the vinyl zinc chloride.

Example 22

Synthesis of 3-tert-butoxy-6-fluorostyrene

The end product was obtained as in Example 1 except that 3-tert-butoxy-6-fluoro-1-iodobenzene was used instead of the 4-tert-butoxy-2,3-difluoro-1-iodobenzene.

Reference Example 1

Synthesis of poly(2,3-difluoro-4-hydroxystyrene)

In a 2-liter flask, 100 g of 2,3-difluoro-4-tert-butoxystyrene was dissolved in 460 ml of toluene. After oxygen was fully purged out of the system, 3.1 g of initiator AIBN was admitted. The flask was heated at 60° C., at which polymerization reaction was effected for 24 hours.

In order to work up the polymer, the reaction mixture was poured into a 4/1 mixture of methanol and water whereupon the polymer precipitated. The polymer was separated and dried, obtaining 90 g of a white polymer, poly(2,3-difluoro-4-tert-butoxystyrene).

The polymer was transferred to a 2-liter flask and dissolved in acetone to form a 15% solution. After the solution was heated at 60° C., and 46 ml of 12N hydrochloric acid was slowly added dropwise, deblocking reaction was effected for 7 hours.

Pyridine, 66 g, was added to the reaction solution, which was concentrated and poured into 5 liters of pure water, whereupon the polymer precipitated. The procedure of dissolving the collected polymer in acetone and pouring into 5 liters of pure water for precipitation was repeated twice. The polymer was separated and dried. There was obtained 81 g of a white polymer, poly(2,3-difluoro-4-hydroxystyrene). This polymer was found to have a weight average molecular weight (Mw) of 8,700 g/mol as measured by the light scattering method and a dispersity (Mw/Mn) of 1.65 as determined from the GPC elution curve.

Reference Example 2

Synthesis of poly(2,6-difluoro-4-hydroxystyrene)

In a 2-liter flask, 100 g of 2,6-difluoro-4-tert-butoxystyrene was dissolved in 460 ml of toluene. After oxygen was fully purged out of the system, 3.1 g of initiator AIBN was admitted. The flask was heated at 60° C., at which polymerization reaction was effected for 24 hours.

In order to work up the polymer, the reaction mixture was poured into a 4/1 mixture of methanol and water whereupon the polymer precipitated. The polymer was separated and dried, obtaining 88 g of a white polymer, poly(2,6-difluoro-4-tert-butoxystyrene).

The polymer was transferred to a 2-liter flask and dissolved in acetone to form a 15% solution. After the solution was heated at 60° C., and 45 ml of 12N hydrochloric acid was slowly added dropwise, deblocking reaction was effected for 7 hours.

Pyridine, 65 g, was added to the reaction solution, which was concentrated and poured into 5 liters of pure water, whereupon the polymer precipitated. The procedure of dissolving the collected polymer in acetone and pouring into 5 liters of pure water for precipitation was repeated twice. The polymer was separated and dried. There was obtained 81 g of a white polymer, poly(2,6-difluoro-4-hydroxystyrene). This polymer was found to have a weight average molecular weight (Mw) of 8,800 g/mol as measured by the light scattering method and a dispersity (Mw/Mn) of 1.67 as determined from the GPC elution curve.

Japanese Patent Application No. 11-253930 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A styrene derivative of formula (1):

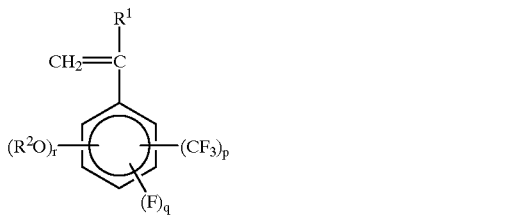

wherein
R$^1$ is hydrogen, a straight, branched or cyclic, unsubstituted or fluoro-substituted alkyl group of 1 to 20 carbon atoms, chlorine atom, or trichloromethyl group,
R$^2$ is methyl, vinyl, allyl, benzyl or a group of formulae (10), (11), (12), (13) and (14):

wherein
R$^3$ is a straight, branched or cyclic alkyl group of 1 to 20 carbon atoms,
R$^4$ and R$^5$ each are hydrogen, a straight, branched or cyclic alkyl group of 1 to 20 carbon atoms which may contain a hetero atom, $R^6$ is a straight, branched or cyclic alkyl group of 1 to 20 carbon atoms which may contain a hetero atom, aryl, aralkyl or oxoalkyl group, and a pair of $R^4$ and $R^5$, a pair of $R^4$ and $R^6$, or a pair of $R^5$ and $R^6$, taken together, may form a cyclic structure of 3 to 12 carbon atoms, $R^7$, $R^8$ and $R^9$ each are a straight, branched or cyclic alkyl group of 1 to 20 carbon atoms which may contain a hetero atom, aryl, aralkyl or oxoalkyl group, and a pair of $R^7$ and $R^8$, a pair of $R^7$ and $R^9$, or a pair of $R^8$ and $R^9$, taken together, may form a cyclic structure of 3 to 12 carbon atoms, $R^{10}$, $R^{11}$ and $R^{12}$ each are a straight or branched alkyl group of 1 to 4 carbon atoms, $R^{13}$ is a straight, branched or cyclic alkyl group of 1 to 20 carbon atoms which may contain a hetero atom, aryl, aralkyl or oxoalkyl group, and "a" is an integer of 0 to 10, p, q and r are integers in the range of $0 \leq p<5$, $0 \leq q<5$, $0<r<5$, and $0<p+q<5$ with the proviso that when $R^2$ is of formula (10) and q is 1, p is not 0.

2. The styrene derivative of claim 1 which is represented by the following formula (2):

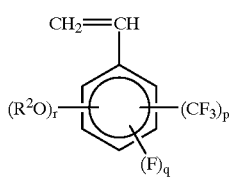
(2)

wherein $R^2$, p, q and r are as defined above.

3. The styrene derivative of claim 2 which is represented by the following formula (3):

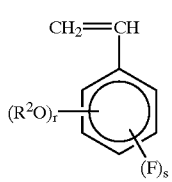
(3)

wherein $R^2$ and r are as defined above and s is an integer in the range of $0<s<5$.

4. The styrene derivative of claim 3 which is represented by the following formula (4):

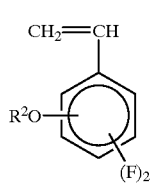
(4)

wherein $R^2$ is as defined above.

5. The styrene derivative of claim 4 which is represented by the following formula (5):

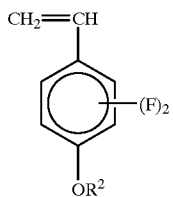
(5)

wherein $R^2$ is as defined above.

6. The styrene derivative of claim 5 which is represented by the following formula (6):

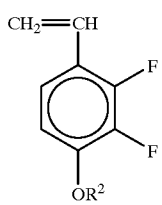
(6)

wherein $R^2$ is as defined above.

7. The styrene derivative of claim 5 which is represented by the following formula (7):

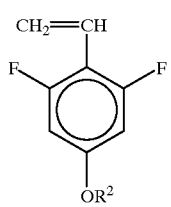
(7)

wherein $R^2$ is as defined above.

8. The styrene derivative of claim 5 which is represented by the following formula (8):

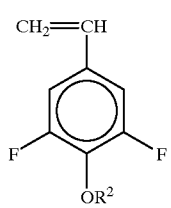
(8)

wherein $R^2$ is as defined above.

9. The styrene derivative of claim 4 which is represented by the following formula (9):

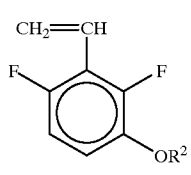
(9)

wherein $R^2$ is as defined above.

10. A styrene derivative according to claim 1, wherein $R^1$ is methyl, ethyl, propyl, isopropyl, n-butyl, sec-butyl, tert-butyl, cyclopentyl, cyclohexyl, 2-ethylhexyl, n-octyl, trifluoromethyl, 2,2,2-trifluoroethyl, 3,3,3-trifluoropropyl, or 1,1,2,3,3-hexafluoropropyl.

11. A styrene derivative according to claim 1, wherein $R^2$ is methyl, vinyl, allyl or benzyl.

12. A styrene derivative according to claim 1, wherein $R^3$ is methyl, ethyl, propyl, isopropyl, n-butyl, sec-butyl, tert-butyl, cyclopentyl, cyclohexyl, 2-ethylhexyl, N-octyl, trifluoromethyl, 2,2,2-trifluoroethyl, 3,3,3-trifluoropropyl, or 1,1,2,3,3-hexafluoropropyl.

13. A compound according to claim 1, wherein $R^2$ is a formula (10) and is selected from acetyl, propionyl, butyryl, and isobutyryl.

14. A styrene derivative according to claim 1, wherein $R^4$ and $R^5$ are each hydrogen, a straight, branched or cyclic alkyl group of 1 to 20 carbon atoms which may contain a heteroatom selected from oxygen, sulphur, nitrogen and fluorine, $R^6$ is a straight, branched or cyclic alkyl group of 1 to 20 carbon atoms which may contain a heteroatom selected from oxygen, sulphur, nitrogen and fluorine, and a pair of $R^4$ and $R^5$, a pair of $R^4$ and $R^6$, or a pair of $R^5$ and $R^6$, taken together, may form a cyclic structure of 3 to 12 carbon atoms.

15. A styrene derivative according to claim 1, wherein $R^2$ is of formula (11) and is selected from methoxymethyl, methoxyethoxymethyl, 1-methoxyethyl, 1-ethoxyethyl, 1-n-propoxyethyl, 1-isopropoxyethyl, 1-n-butoxyethyl, 1-isobutoxyethyl, 1-sec-butoxyethyl, 1-tert-butoxyethyl, 1-tert-amyloxyethyl, 1-ethoxy-n-propyl, 1-cyclopentyloxyethyl, 1-cyclohexyloxyethyl, 1-methoxy-n-propyl, ethoxypropyl, 1-methoxy-1-methyl-ethyl, 1-ethoxy-1-methyl-ethyl, tetrahydrofuran-2-yl, 2-methyltetrahydrofuran-2-yl, tetrahydropyran-2-yl and 2-methyltetrahydropyran-2-yl.

16. A styrene derivative according to claim 1, wherein $R^7$, $R^8$ and $R^9$ are each a straight, branched or cyclic alkyl group of 1 to 20 carbons atoms which may contain a heteroatom selected from oxygen, sulphur, nitrogen and fluorine, and a pair of $R^7$ and $R^8$, a pair of $R^7$ and $R^9$ or a pair of $R^8$ and $R^9$, taken together, can form a cyclic structure of 3 to 12 carbon atoms.

17. A styrene derivative according to claim 1, where $R^2$ is a formula (12) and is selected from tert-butyl, triethylcarbyl, 1-ethylnorbornyl, 1-methylcyclohexyl, 1-ethylcyclopentyl, 2-(2-methyl)adamantyl, 2-(2-ethyl) adamantyl, and tert-amyl.

18. A styrene derivative according to claim 1, wherein $R^{10}$, $R^{11}$ and $R^{12}$ are each independently methyl, ethyl, propyl, isopropyl, n-butyl, sec-butyl, or tert-butyl.

19. A styrene derivative according to claim 1, wherein $R^2$ is a formula (13) and is selected from trimethylsilyl, triethylsilyl and tert-butyldimethylsilyl.

20. A styrene derivative according to claim 1, wherein $R^2$ is a formula (14) and is selected from tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl, 2-tetrahydrofuranyloxycarbonylmethyl, triethylcarbyloxycarbonylmethyl, 1-ethylnorbornyloxycarbonylmethyl, 1-methylcyclohexyloxycarbonylmethyl, 1-ethylcyclohexyloxycarbonylmethyl, 1-methylcyclopentyloxycarbonylmethyl, 1-ethylcyclopentyloxycarbonylmethyl, 2-(2-methyl) adamantyloxycarbonylmethyl, 2-(2-ethyl) adamantyloxycarbonylmethyl, and tert-amyloxycarbonylmethyl.

21. A styrene derivative of formula (1):

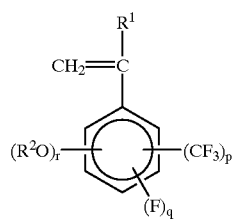

(1)

wherein $R^1$ is hydrogen, a straight, branched or cyclic, unsubstituted or fluoro-substituted alkyl group of 1 to 20 carbon atoms, chlorine atom, or trichloromethyl group, $R^2$ is is methyl, vinyl, allyl, benzyl or a group of formulae (10), (11), (12), (13) and (14):

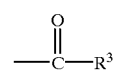

(10)

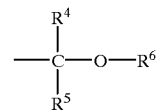

(11)

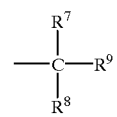

(12)

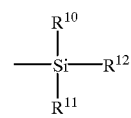

(13)

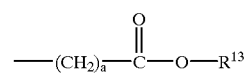

(14)

wherein $R^3$ is a straight, branched or cyclic alkyl group of 1 to 20 carbon atoms, $R^4$ and $R^5$ each are hydrogen, a straight, branched or cyclic alkyl group of 1 to 20 carbon atoms which may contain a hetero atom, $R^6$ is a straight, branched or cyclic alkyl group of 1 to 20 carbon atoms which may contain a hetero atom, aryl, aralkyl or oxoalkyl group, and a pair of $R^4$ and $R^5$, a pair of $R^4$ and $R^6$, or a pair of $R^5$ and $R^6$, taken together, may form a cyclic structure of 3 to 12 carbon atoms, $R^7$, $R^8$ and $R^9$ each are a straight, branched or cyclic alkyl group of 1 to 20 carbon atoms which may contain a hetero atom, aryl, aralkyl or oxoalkyl group, and a pair of $R^7$ and $R^8$, a pair of $R^7$ and $R^9$, or a pair of $R^8$ and $R^9$, taken together, may form a cyclic structure of 3 to 12 carbon atoms, $R^{10}$, $R^{11}$ and $R^{12}$ each are a straight or branched alkyl group of 1 to 4 carbon atoms, $R^{13}$ is a straight, branched or cyclic alkyl group of 1 to 20 carbon atoms which may contain a hetero atom, aryl, aralkyl or oxoalkyl group, and "a" is an integer of 0 to 10, and p, q an r are integers in the range of $0 \leq p<5$, $2 \leq q<5$, $0<r<5$, and $0<p+q<5$.

22. A styrene derivative according to claim 1, wherein q is 2 and r is 1.

23. A styrene derivative according to claim 21, wherein q is 2 and r is 1.

24. A styrene derivative according to claim 1, wherein $R^4$ and $R^5$ are each H, straight, branched or cyclic alkyl group of 1 to 20 carbon atoms which may contain a heteroatom selected from oxygen, sulphur, nitrogen and fluorine, $R^6$ is a straight, branched or cyclic alkyl group of 1 to 20 carbon atoms which may contain a heteroatom selected from oxygen, sulphur, nitrogen and fluorine, and a pair of $R^4$ and $R^5$, a pair of $R^4$ and $R^6$, or a pair of $R^5$ and $R^6$, together taken, can also form a cyclic structure of 3 to 12 carbon atoms, $R^7$, $R^8$ and $R^9$ are each a straight, branched or cyclic alkyl group of 1 to 20 carbon atoms which may contain a heteroatom selected from oxygen, sulphur, nitrogen and fluorine, and a pair of $R^7$ and $R^8$, a pair of $R^7$ and $R^9$, or a pair of $R^8$ and $R^9$, taken together, can also form a cyclic structure of 3 to 12 carbon atoms, $R^{13}$ is a straight, branched or cyclic alkyl group of 1 to 20 carbon atoms which may contain a heteroatom selected from oxygen, sulphur, nitrogen and fluorine, $R^6$, $R^7$, $R^8$, $R^9$ and $R^{13}$ can also be an aryl group of 6–20 carbon atoms which is unsubstituted or substituted by methyl, ethyl or methoxy, an araalkyl group of 7–20 carbon atoms, an oxoalkyl group of 4 to 20 carbon atoms, or a group of the following subformulas

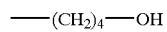 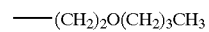

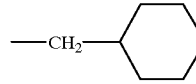 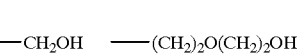

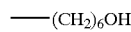 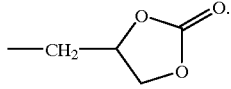

25. A styrene derivative according to claim 21, wherein $R^4$ and $R^5$ are each H, straight, branched or cyclic alkyl group of 1 to 20 carbon atoms which may contain a heteroatom selected from oxygen, sulphur, nitrogen and fluorine, $R^6$ is a straight, branched or cyclic alkyl group of 1 to 20 carbon atoms which may contain a heteroatom selected from oxygen, sulphur, nitrogen and fluorine, and a pair of $R^4$ and $R^5$, a pair of $R^4$ and $R^6$, or a pair of $R^5$ and $R^6$, together taken, can also form a cyclic structure of 3 to 12 carbon atoms, $R^7$, $R^8$ and $R^9$ are each a straight, branched or cyclic alkyl group of 1 to 20 carbon atoms which may contain a heteroatom selected from oxygen, sulphur, nitrogen and fluorine, and a pair of $R^7$ and $R^8$, a pair of $R^7$ and $R^9$, or a pair of $R^8$ and $R^9$, taken together, can also form a cyclic structure of 3 to 12 carbon atoms, $R^{13}$ is a straight, branched or cyclic alkyl group of 1 to 20 carbon atoms which may contain a heteroatom selected from oxygen, sulphur, nitrogen and fluorine, $R^6$, $R^7$, $R^8$, $R^9$ and $R^{13}$ can also be an aryl group of 6–20 carbon atoms which is unsubstituted or substituted by methyl, ethyl or methoxy, an araalkyl group of 7–20 carbon atoms, an oxoalkyl group of 4 to 20 carbon atoms, or a group of the following subformulas

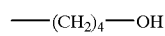 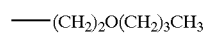

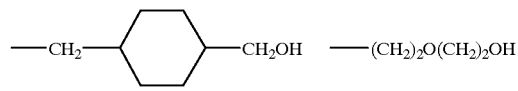

 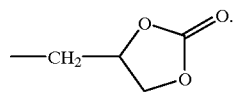

* * * * *